United States Patent [19]

Fujita et al.

[11] Patent Number: 4,659,451
[45] Date of Patent: Apr. 21, 1987

[54] REFERENCE ELECTRODE FOR HIGH PRESSURE LIQUID

[75] Inventors: Isao Fujita; Takashi Shirai, both of Kyoto, Japan

[73] Assignee: Horiba, Ltd., Kyoto, Japan

[21] Appl. No.: 759,435

[22] Filed: Jul. 26, 1985

[30] Foreign Application Priority Data

Aug. 30, 1984 [JP] Japan ............................ 59-132485[U]

[51] Int. Cl.$^4$ ............................................ G01N 27/30
[52] U.S. Cl. .................................... 204/435; 204/408
[58] Field of Search ................................ 204/435, 408

[56] References Cited

U.S. PATENT DOCUMENTS

| | | | |
|---|---|---|---|
| 2,595,042 | 4/1952 | Wyllie | 204/435 |
| 3,410,779 | 11/1968 | Whitehead et al. | 204/435 |
| 3,445,366 | 5/1969 | Vermeer | 204/435 |
| 3,463,717 | 8/1969 | Koopman et al. | 204/435 |
| 3,652,439 | 3/1972 | Ben-Yaakov et al. | 204/435 |
| 3,767,552 | 10/1973 | Lauer | 204/415 |
| 4,061,117 | 12/1977 | Ikeura | 204/428 |
| 4,128,468 | 12/1978 | Bukamier | 204/435 |
| 4,273,637 | 6/1981 | MacDonald | 204/435 |
| 4,383,907 | 5/1983 | Legrand et al. | 204/426 |

Primary Examiner—T. Tung
Attorney, Agent, or Firm—Wenderoth, Lind & Ponack

[57] ABSTRACT

A reference electrode for use in testing liquid at a high pressure, has an internal liquid containing body having an internal liquid containing space therein and a liquid-junction one side of which is exposed to the high pressure liquid to be tested and the other side of which is exposed to the internal liquid contained in the internal liquid containing space. A reference electrode body surrounds the internal liquid containing body and defines a pressure compensating space between the internal liquid containing body and the inside of the reference electrode body, the pressure compensating space being open outwardly of the reference electrode body at a part there of which is exposed to the high pressure liquid to be tested when the reference electrode is in position for normal use, the pressure compensating space receiving the high pressure liquid to be tested therein. A flexible bellows is provided between the spaces and in liquid tight engagement with the internal liquid containing body for compensating for the pressure of the high pressure liquid to be tested on the internal liquid through the liquid-junction.

1 Claim, 2 Drawing Figures

REFERENCE ELECTRODE FOR HIGH PRESSURE LIQUID

BACKGROUND OF THE INVENTION

1. Field of the Invention

The present invention relates to a reference electrode used for measuring the concentration of various kinds of ions in a liquid by combining it with various kinds of ion electrodes, more specifically to a reference electrode for use at high pressure and comprising a liquid-junction contacting a liquid to be tested and which is at high pressure, a space which is open to said liquid-junction and housing an internal solution therein, and a further space which is open to the liquid to be tested for compensating for the pressure of the liquid to be tested.

2. Description of the Prior Art

It is a well-known practice, where a liquid to be tested is under pressure, for example the primary cooling water of a nuclear reactor, to introduce the liquid to be tested into an internal solution through a liquid-junction to reduce the concentration of said internal solution, whereby an electric potential is changed.

One of the disadvantages of such a practice is that pressure compensation must be carried out by holding the space for containing said internal solution under the same high pressure as that of the liquid to be tested. Various means for pressure compensation have been proposed and put into operation. A typical one has a construction as shown in FIG. 2.

Referring now to FIG. 2, this conventional reference electrode comprises a body 1, a cylindrical body 4 fixedly mounted in said body 1 and enclosing a space 3 for containing the internal solution therein, and a liquid-junction 5 formed in a portion of said cylindrical body 4 which projects out of said body 1. A space 6 is left between said cylindrical body 4 and said body 1 for receiving a liquid to be tested, the liquid to be tested being admitted into a pressure compensating space 7 within said body 4 through said space 6 and openings 4a in body 4. A piston 18 is slidably inserted in said cylindrical body 4, and an O-ring 19 is provided around said piston 18 and against the inside surface of said cylindrical body 4 and between said piston 18 and an internal electrode A, respectively extending through said piston 18 into said space 3, said space 3 containing an internal solution. The space 3 and space 7 are thus separated from each other by said piston 18.

Accordingly, when this reference electrode has the projecting portion of cylindrical body 4 inserted in the liquid to be tested which is at high pressure, for example by threading the threaded end 1a of body 1 into a threaded opening in a conduit for the liquid to be tested, the liquid to be tested is introduced into said space 7 through said space 6 and opening 4a for moving the piston 18 for holding the pressure inside said space 3 in which the internal solution is contained at the same high level as that of the liquid to be tested.

However, in this conventional reference electrode, since the pressure compensation is carried out by sliding said piston 18 relative to the body 1 and the cylindrical body 4, the liquid to be tested cannot be completely prevented from being introduced into said internal solution in the space 3 past the piston 18, thereby producing an error in the measurement made by electrode A. This occurs even though the O-rings 19 are provided. In addition, this conventional reference electrode has many other disadvantages. For example, the smooth sliding of said piston 18 is increasingly obstructed whereby it takes a long time for the pressure compensation if an effort for preventing said liquid to be tested from being introduced into said internal solution is made.

OBJECT AND BRIEF SUMMARY OF THE INVENTION

The present invention seeks to eliminate the above described disadvantages.

Thus it is an object of the present invention to provide a reference electrode for testing high pressure liquids, which electrode is capable of completely preventing the liquid to be tested from being introduced into the internal solution and which is also capable of compensating for the pressure of the liquid to be tested in a short time, yet which reference electrode has a relatively simple construction.

In order to achieve this object, the present invention provides a reference electrode for use in testing liquid at a high pressure, comprising: an internal liquid containing body having an internal liquid containing space therein and a liquid-junction one side of which is exposed to the high pressure liquid to be tested and the other side of which is exposed to the internal liquid contained in said internal liquid containing space; a reference electrode body surrounding said internal liquid containing body and defining a pressure compensating space between said internal liquid containing body and the inside of said reference electrode body, said pressure compensating space being open outwardly of said reference electrode body at a part thereof which is exposed to the high pressure liquid to be tested when the reference electrode is in position for normal use, said pressure compensating space receiving the high pressure liquid to be tested therein; and a flexible bellows between said spaces and in liquid tight engagement with said internal liquid containing body for compensating for the pressure of the high pressure liquid to be tested on the internal liquid through said liquid-junction. Thus, when a high pressure liquid to be tested is introduced into said pressure compensating space, this flexible bellows is deformed at once and the deformation of this bellows accomplishes the pressure compensation. By this means, the pressure compensation can be carried out in a short time. In addition, since sliding of a piston does not occur, as in the conventional reference electrode, the liquid to be tested can be completely prevented from being introduced into the internal solution.

DETAILED DESCRIPTION OF THE PREFERRED EMBODIMENT

Figure 1:
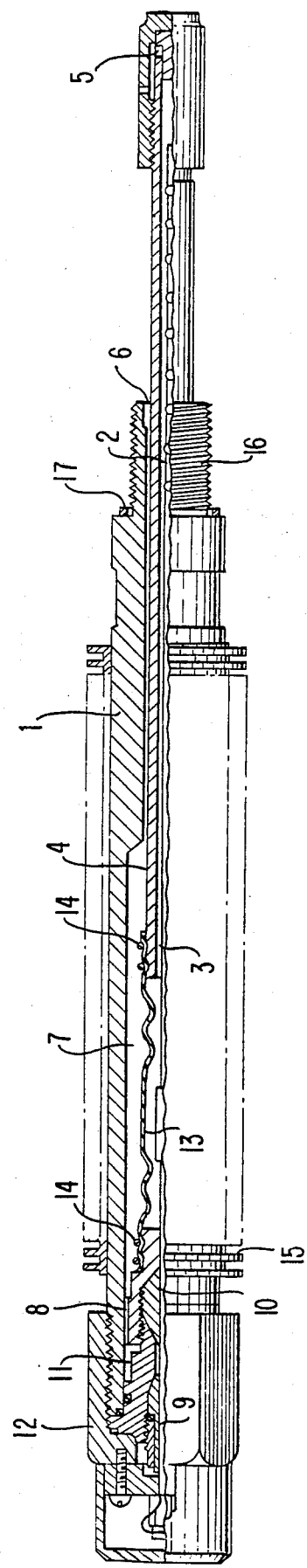
FIG. 1 is a vertically sectioned side view of a reference electrode for a high pressure liquid to be tested according to the present invention.
Figure 2:
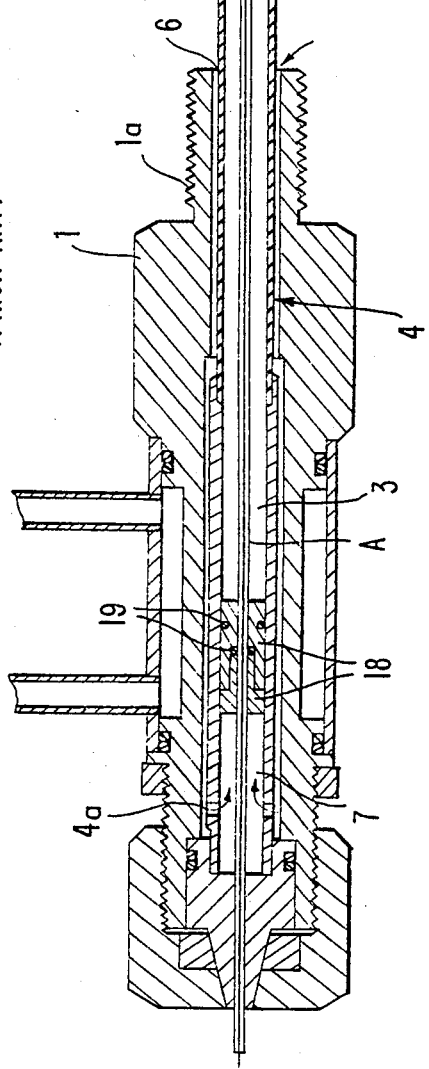
FIG. 2 is a vertically sectioned side view showing a conventional reference electrode.

Referring to FIG. 1, the reference electrode according to the invention comprises a reference electrode body 1, a cylindrical body 4 mounted therein and forming a space 3 for containing the internal solution therein and having an internal electrode 2 extending therethrough. The cylindrical body 4 is provided with a liquid-junction 5 at the end of a portion of cylindrical body 4, projecting from body 1, the liquid-junction contacting a liquid to be tested. A space 6 is left between said cylindrical body 4 where it projects out of said body 1 and said body 1 for receiving the liquid to be tested and a pressure compensating space 7 for compensating for the pressure of the liquid to be tested is formed inside said body 1 into which said space 6 opens. A nozzle 8 is fixedly mounted on the inside of said body 1 by a sleeve 9, a busing 10, a sleeve-holder 11, and a cap 12 and a cylindrical flexible bellows 13 extends from said nozzle 8 to said cylindrical body 4, and said flexible bellows 13 is fixedly mounted on said nozzle 8 and said cylindrical body 4, respectively, by means of a suitable means such as a clip 14 in a liquid tight manner. Heat radiating fins 15 corresponding to said space 7 for compensating the pressure, are fixedly mounted on the outside of said body 1 by means of conductive adhesive compounds or the like along a length of the body 1 and in a position nearly corresponding to that of said pressure compensating space 7 for radiating heat from said body 1. In addition a threaded end 16 is provided on body 1 for threading the body 1 into a liquid conduit or the like and a metallic O-ring 17 is provided around end 16.

When this high pressure liquid testing reference electrode is mounted on, for example, the primary cooling water tank (not shown) of a nuclear reactor by threading said threaded end 16 into a threaded aperture in said tank, high pressure cooling water, which is the liquid to be tested, at a pressure of about 82 kg/cm$^2$ is introduced into said pressure compensating space 7 through said space 6. Thereupon, said flexible bellows 13 is deformed at once by this high pressure liquid, whereby the pressure of the internal solution inside said space 3 is made substantially the same as that of the cooling water thus balancing the pressure of the cooling water on the liquid-junction 5. Although the primary cooling water of a nuclear reactor has a temperature of about 296° C., the body 1 around said pressure compensating space 7 is effectively cooled by the action of said heat radiating fins 15, whereby the destruction of said bellows due to the high temperature can be prevented. In addition, such disadvantages as errors in measurement are prevented.

As is clear from the above description, since the reference electrode according to the present invention utilizes flexible bellows as a means for compensating for the pressure of the liquid to be tested on the liquid-junction, the time required for compensating for the pressure can be remarkably shortened in comparison with the conventional electrode utilizing a piston, and simultaneously the liquid being tested can be positively prevented from being introduced into the internal solution past the pressure compensating bellows.

What is claimed is:

1. A reference electrode for use in testing a high temperature liquid at a high pressure, comprising:

an elongated small diameter internal liquid containing body having an internal liquid containing space therein and a liquid junction one side of which is exposed to the high pressure liquid to be tested and the other side of which is exposed to the internal liquid contained in said internal liquid containing space;

elongated reference electrode body surrounding a portion of the length of said internal liquid containing body remote from said liquid junction and defining an elongated pressure compensating space between said internal liquid containing body and the inside of said reference electrode boy, said pressure compensating space being open outwardly of said reference electrode body toward said liquid junction at a part thereof which is exposed to the high pressure liquid to be tested when the reference electrode is in position for normal use, said pressure compensating space receiving the high pressure liquid to be tested therein;

an elongated annular flexible bellows between said spaces and in liquid tight engagement with said internal liquid containing body for compensating for the pressure of the high pressure liquid to be tested on the internal liquid through said liquid junction; and heat dissipating fins on the part of said reference electrode body around said bellows for radiating heat from high temperature liquid in said elongated pressure compensating space for preventing destruction of said bellows due to heat.

* * * * *